(12) United States Patent
Welch et al.

(10) Patent No.: US 9,808,549 B2
(45) Date of Patent: Nov. 7, 2017

(54) SYSTEM FOR DETECTING STERILE FIELD EVENTS AND RELATED METHODS

(71) Applicant: UNIVERSITY OF CENTRAL FLORIDA RESEARCH FOUNDATION, INC., Orlando, FL (US)

(72) Inventors: Gregory Welch, Longwood, FL (US); Arjun Nagendran, Orlando, FL (US); Jason Hochreiter, Cocoa, FL (US); Laura Gonzalez, Tampa, FL (US); Hassan Foroosh, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 25 days.

(21) Appl. No.: 14/757,450

(22) Filed: Dec. 23, 2015

(65) Prior Publication Data

US 2016/0184469 A1 Jun. 30, 2016

Related U.S. Application Data

(60) Provisional application No. 62/096,619, filed on Dec. 24, 2014.

(51) Int. Cl.
| | |
|---|---|
| *H04N 5/228* | (2006.01) |
| *H04N 7/18* | (2006.01) |
| *A61L 2/28* | (2006.01) |
| *G06K 9/00* | (2006.01) |
| *A61B 5/00* | (2006.01) |

(52) U.S. Cl.
CPC ............... *A61L 2/28* (2013.01); *A61B 5/002* (2013.01); *G06K 9/00771* (2013.01); *H04N 7/183* (2013.01); *A61L 2202/14* (2013.01)

(58) Field of Classification Search
CPC ................................. H04N 5/228; H04N 7/18
USPC .......... 348/143, 154, 155, 161, 169, 208.14, 348/208.15
See application file for complete search history.

(56) References Cited

U.S. PATENT DOCUMENTS

| | | |
|---|---|---|
| 4,850,716 A | 7/1989 | Baker et al. |
| 5,732,712 A | 3/1998 | Adair |

(Continued)

OTHER PUBLICATIONS

Chan et al. "Virtual Reality Simulation in Neurosurgery: Technologies and Evolution" Neurosurgery (2013) 72 (suppl_1): Jan. 1, 2013 A154-A164. Abstract Only.

(Continued)

*Primary Examiner* — Daquan Zhao
(74) *Attorney, Agent, or Firm* — Allen, Dyer, Doppelt & Gilchrist, P.A.

(57) ABSTRACT

A system is for monitoring a sterile field associated with a medical procedure. The system may include a sensor being adjacent an area where the medical procedure is to be performed. The sensor is configured to monitor at least the area, a patient for the medical procedure, and a medical technician for the medical procedure. The system may include a processor coupled to the sensor and configured to detect a sterile field event, and an associated location for the sterile field event, and an output device coupled to the processor and configured to generate an alert indicator when the sterile field event is detected, the alert indicator also including the associated location.

19 Claims, 8 Drawing Sheets

(56) References Cited

U.S. PATENT DOCUMENTS

| | | |
|---|---|---|
| 5,873,814 A | 2/1999 | Adair |
| 5,970,980 A | 10/1999 | Adair |
| 6,132,367 A | 10/2000 | Adair |
| 7,853,311 B1 | 12/2010 | Webb |
| 2008/0147089 A1 | 6/2008 | Loh et al. |
| 2008/0312529 A1 | 12/2008 | Amiot et al. |
| 2012/0154582 A1* | 6/2012 | Johnson ............... G06F 19/321 348/143 |

OTHER PUBLICATIONS

Reiley et al. "Review of methods for objective surgical skill evaluation" Surgical Endoscopy 25(2): Feb. 2011; pp. 356-366.

Basdogan et al. "VR-Based Simulators for Training in Minimally Invasive Surgery" IEEE Computer Graphics and Applications 27(2): Mar. 2007; pp. 54-66.

Liu et al. "A Survey of Surgical Simulation: Applications, Technology, and Education" Presence, vol. 12, No. 6, Dec. 2003, pp. 599-614.

\* cited by examiner

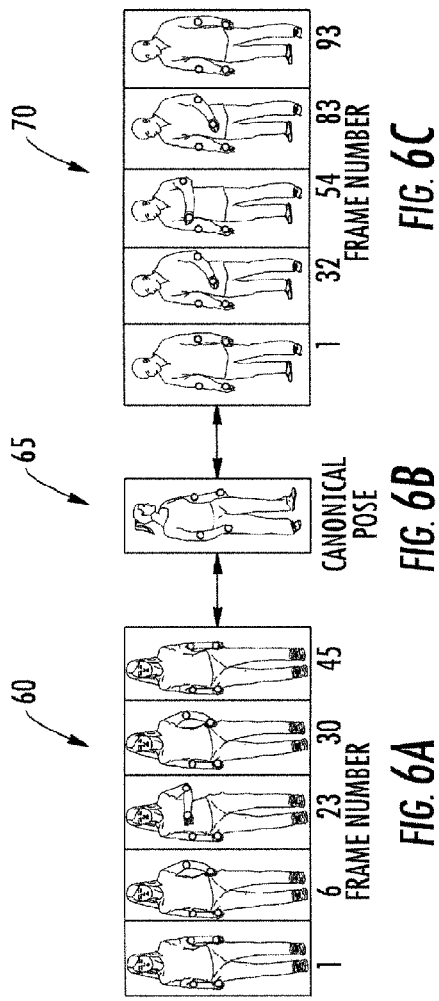
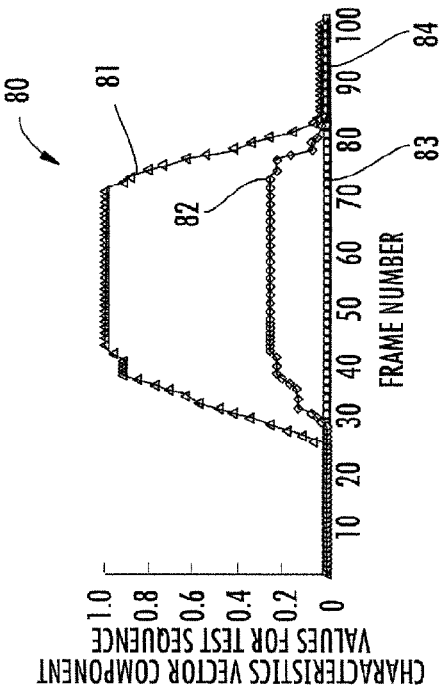
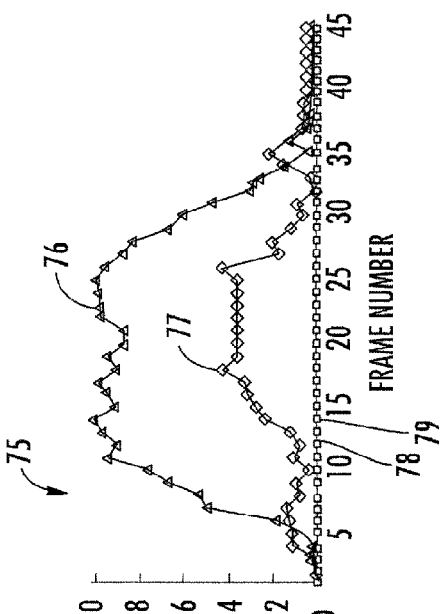
FIG. 6A
FIG. 6B
FIG. 6C
FIG. 7A
FIG. 7B

SYSTEM FOR DETECTING STERILE FIELD EVENTS AND RELATED METHODS

RELATED APPLICATION

This application is based upon prior filed Application No. 62/096,619 filed Dec. 24, 2014, the entire subject matter of which is incorporated herein by reference in its entirety.

TECHNICAL FIELD

The present disclosure relates to the field of medical systems, and, more particularly, to a system for monitoring a sterile field and related methods.

BACKGROUND

In any medical procedure where infection is possible, it is critical for medical personnel to be aware of and to protect the sterile field. The sterile field is an area that is considered free of microorganisms, such as bacteria and viruses. During the medical procedure, medical personnel adhere to a set of rules (or "best practices") for protecting the sterile field. For example, the rules may require medical personnel to not touch sterile supplies with ungloved hands or other non-sterile objects (including parts of the patient), and may require medical personnel to thoroughly wash their hands before gloving.

As is typical with human behavior in general, and in particular in complex interactions between medical personnel and patients, it is not uncommon for medical personnel to violate rules due to error, or risk violating the rules for example due to rushing in emergency situations or simply poor habits. In some other situations where human error can have grave consequences, automated systems have been developed to help monitor the conditions and alert the human under risky/dangerous circumstances. Examples include collision avoidance systems for aircraft and automobiles. Similarly, for certain medical procedures, there is a need to automatically monitor the sterile field, including objects and humans in or proximal to that field, and alert the medical personnel if non-sterile objects come in contact with sterile objects or the sterile field, or risk coming into contact with sterile objects or the sterile field, for example due to close proximity of the objects.

SUMMARY

Generally speaking, a system for monitoring a sterile field associated with a medical procedure. The system may include at least one sensor being adjacent an area where the medical procedure is to be performed. The at least one sensor may be configured to monitor at least the area, a patient for the medical procedure, and a medical technician for the medical procedure. The system may include a processor coupled to the at least one sensor and configured to detect a sterile field event or risky conditions, and an associated location for the sterile field event/conditions, and an output device coupled to the processor and configured to generate an alert indicator when the sterile field event is detected, the alert indicator also including the associated location.

In some embodiments, the at least one sensor may comprise an image sensor configured to generate at least one of image data and depth data for the sterile field event. The system may also include at least one "tag" (e.g. NFC or optical tags) coupled to at least one of a device associated with the medical procedure, the patient, and the medical technician, and the at least one sensor may be configured to detect a location of the at least one of the device associated with the medical procedure, the patient, and the medical technician.

Additionally, the processor may be configured to generate a spatial model of the area to assist in the automated monitoring, the spatial model comprising a plurality of elements such as surfaces, objects, locations, and the like. The processor may be configured to generate a contamination probability value for each element of the spatial model. For example, the output device comprises a display, and the processor may be configured to generate indicators of elements having respective contamination probability values exceeding a threshold on the display.

The processor may be configured to iteratively update the contamination probability value for each element of the spatial model during the medical procedure. The processor may also be configured to generate a gap value (e.g., a distance) between adjacent elements in the plurality of elements of the spatial model, and when one of the adjacent elements is contaminated and the gap value is less than a threshold gap value, indicate the other element also as (likely) contaminated. The processor may be configured to detect the sterile field event comprising at least one of a violation (e.g., a gap decreasing below a threshold) and a significant risk of violation of the sterile field (e.g., contamination probability exceeding a threshold).

Another aspect is directed to a method for operating a system for monitoring a sterile field associated with a medical procedure. The method may include operating at least one sensor being adjacent an area where the medical procedure is to be performed and to monitor at least the area, a patient for the medical procedure, and a medical technician for the medical procedure, and operating a processor coupled to the at least one sensor and to detect a sterile field event (including, for example, exceeding/falling below any distance or probability tolerance threshold), and an associated location for the sterile field event. The method may include operating an output device coupled to the processor and to generate an alert indicator when the sterile field event is detected, the alert indicator also including the associated location.

BRIEF DESCRIPTION OF THE DRAWINGS

FIGS. 6A-6C are images for modeling of people in the system of FIG. 1.

FIGS. 7A-7B are diagrams of spacing variances in the system of FIG. 1.

DETAILED DESCRIPTION

Figure 1:
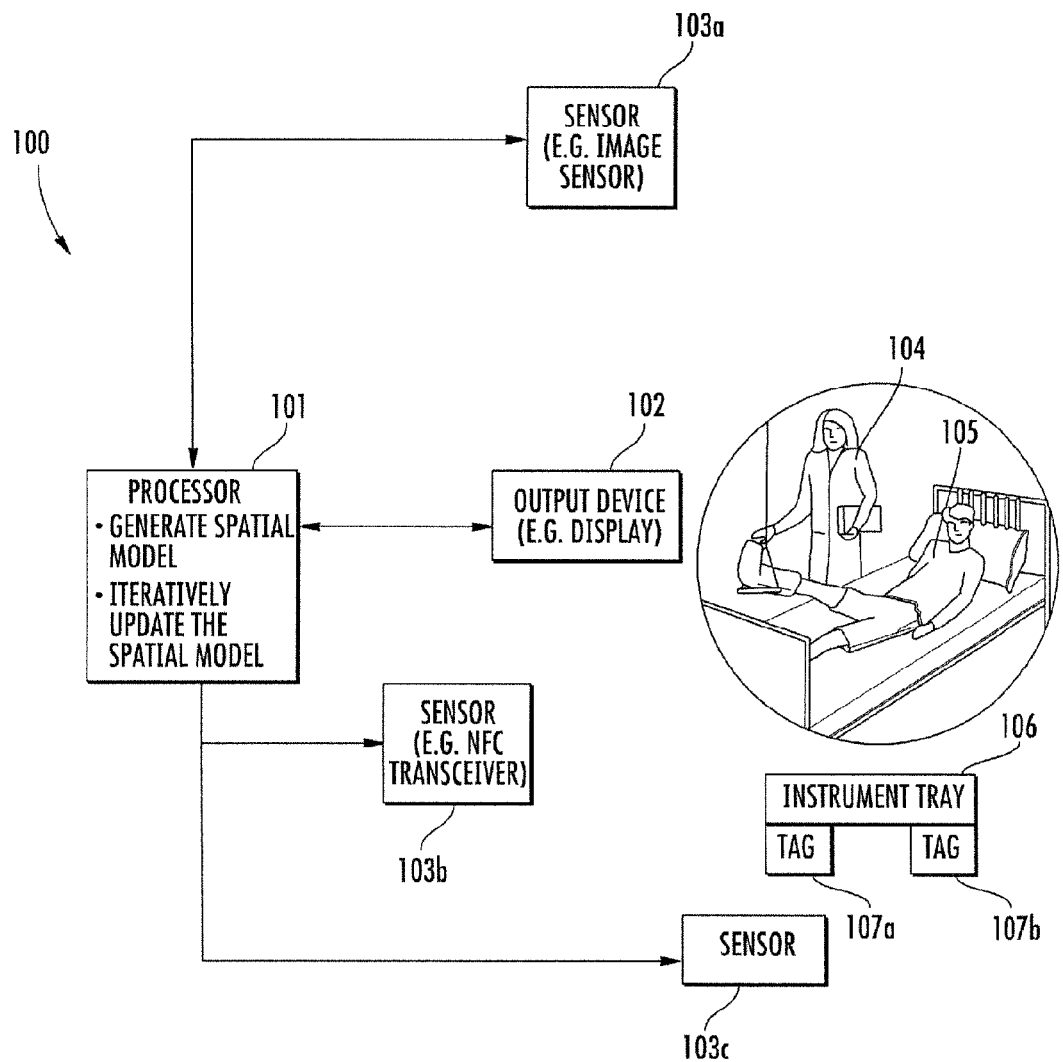
FIG. 1 is a schematic diagram of a system, according to the present disclosure.
Figures 2A, 2B:
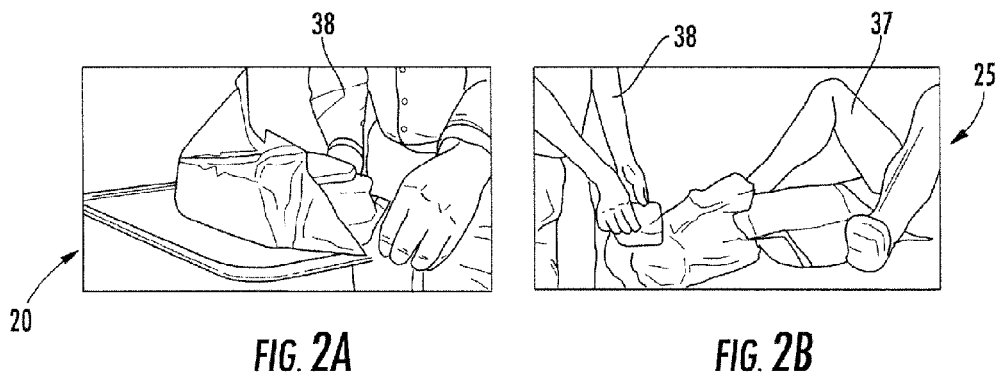
FIGS. 2A-2D and 3 are images of a training procedure for catheter insertion, according to the present disclosure.
Figures 2C, 2D:
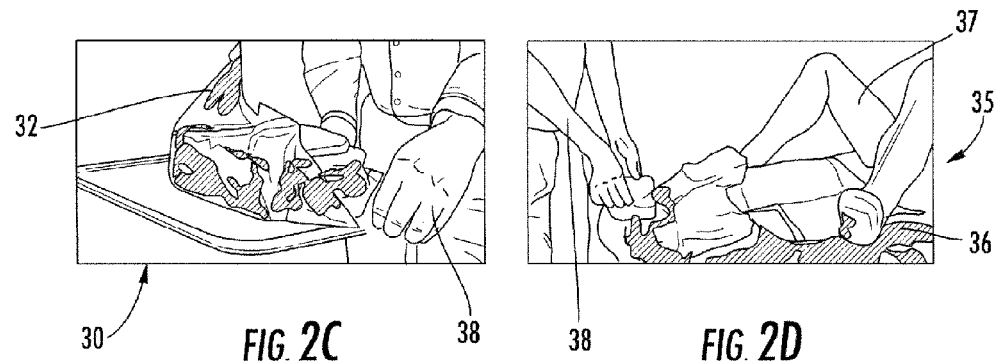
Figure 3:
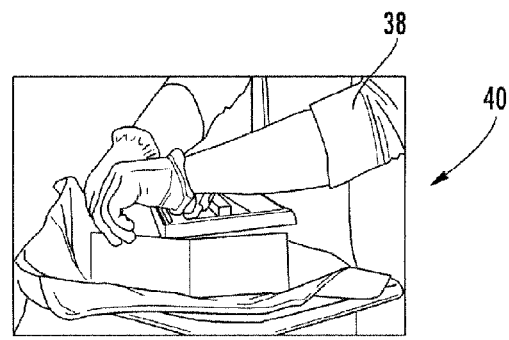
Figure 4:
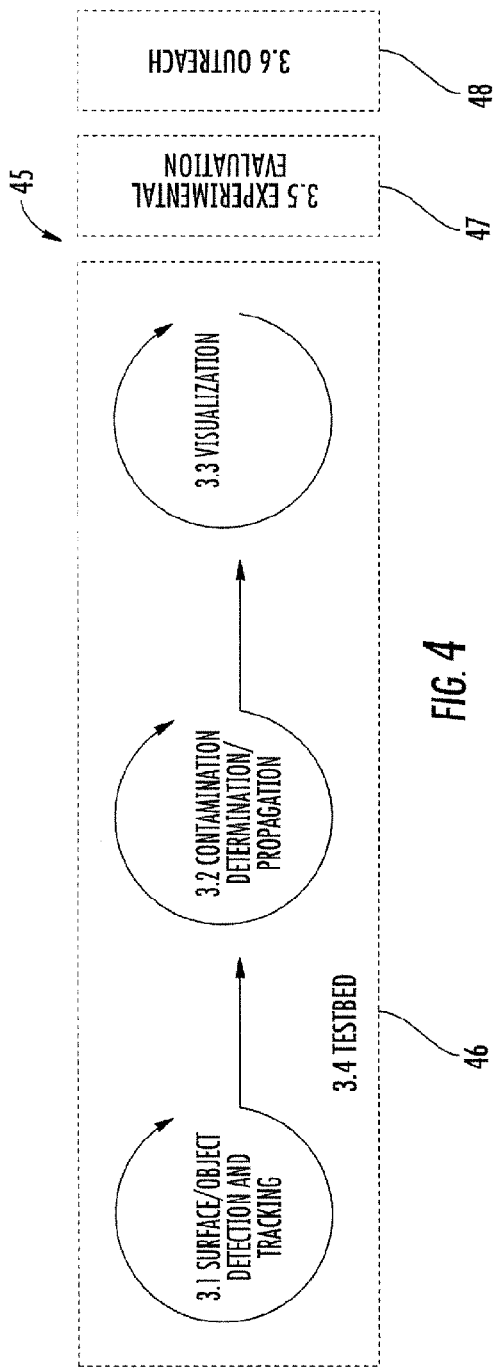
FIG. 4 is a flowchart illustrating operation of the system of FIG. 1.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

Generally, we disclose a system is for monitoring a sterile field associated with a medical procedure. The system comprises at least one sensor being adjacent an area where the medical procedure is to be performed. The at least one sensor may be for monitoring the area, a patient for the medical procedure, and a medical technician for the medical procedure. The system may include a processor coupled to the at least one sensor and for detecting a violation of the sterile field with an associated location for the violation, for detecting a near-violation/behavior risking violation of the sterile field, with an associated location for the near-violation/risky behavior, and an output device coupled to the processor and generating an alert indicator when the violation/risk is detected, the alert indicator also including the associated locations of the violation/risk.

The at least one sensor may comprise an image sensor generating image data or depth data for the violation of the sterile field. The system may further comprise at least one of a visible, an acoustic, a near field communications (NFC), or another passive/active tag or marker coupled to at least one of a device, an object, or a human associated with the medical procedure.

The processor may generate a spatial model of the area, the spatial model comprising a plurality of elements such as surfaces, objects, locations, and the like. The processor may generate a contamination probability value for each spatial element. The output device may comprise a display, and the processor may generate indicators of elements having respective contamination probability values exceeding a threshold on the display. The processor may iteratively update the contamination probability value for each element during the medical procedure. The processor may generate a gap value (e.g., a distance) between adjacent elements in the plurality of elements of the spatial model. The processor may also, when one of the adjacent elements is contaminated and the gap value is less than a threshold gap value, indicate the other element also as contaminated. The processor may also iteratively evaluate the risk of contamination over time and space, due to for example repeated close/proximal encounters between sterile and non-sterile objects/people. The processor may also, when risky behavior is identified, indicate the nature of the behavior and any elements potentially contaminated.

Another aspect is directed to a method for operating a system for monitoring a sterile field associated with a medical procedure. The method may include operating at least one sensor adjacent an area where the medical procedure is to be performed, the at least one sensor for monitoring the area, a patient for the medical procedure, and a medical technician for the medical procedure, and operating a processor coupled to the at least one sensor and for detecting a violation of the sterile field, or associated risky behavior, and an associated location for the violation/risk. The method may further include operating an output device coupled to the processor and for generating an alert indicator when the violation/risk is detected, the alert indicator also including the associated location.

Referring specifically to FIG. 1, an example system 100 for monitoring a sterile field associated with a medical procedure (e.g. the illustrated catheter insertion). The system 100 illustratively includes a plurality of sensors 103a-103c being adjacent an area where the medical procedure is to be performed. The plurality of sensors 103a-103c is for monitoring at least the area, a patient 105 for the medical procedure, and a medical technician 104 for the medical procedure. It should be appreciated that the plurality of sensors 103a-103c can monitor more personnel than the illustrated patient 105 and single medical technician 104 (e.g. a plurality of medical technicians).

The system 100 illustratively includes a processor 101 coupled to the plurality of sensors 103a-103c for detecting a sterile field event. The sterile field event may comprise one or more of a violation of the sterile field (e.g. touching the sterile field with an unsterile object), an event with a threshold possibility of breaking the sterile field (e.g. the unsterile object breaking a minimum spacing of the sterile field), such as risky behavior, and an associated location for the sterile field event.

In essence, the system 100 is monitoring the behavior of the medical technician 104 and looking for actions that cause a sterile field event (including risky behavior). In other words, the system 100 is detecting when an event exceeds a threshold risk of contamination (e.g. contaminated touching in the sterile field or threshold proximity that is equated with touching the sterile field).

The system 100 illustratively includes an output device 102 coupled to the processor 101 and generating an alert indicator when the sterile field event is detected, the alert indicator also including the associated location of the sterile field event. Accordingly, when the medical technician 104 possibly violates the sterile field, the medical technician is alerted and provided a location of the sterile field event.

The plurality of sensors 103a-103c may include an image sensor generating image data or depth data for the violation of the sterile field. For example, the image sensor may comprise a camera and/or an infrared source/sensor. In the illustrated embodiment, the system 100 further comprises a plurality of tags (e.g. NFC or optical tags) 107a-107b coupled to at least one device (e.g. instruments, trays 106, medical devices, etc.) associated with the medical procedure, and the plurality of sensors 103a-103c may comprise a transceiver (e.g. an NFC transceiver) detecting when the at least one device violates the sterile field. In some embodiments, the NFC tag may be replaced with a visible or acoustic or other active/passive tag or marker.

In some embodiments, the processor 101 may generate a spatial model of the area, the spatial model comprising a plurality of elements. The plurality of elements may comprise geometric surfaces, geometric objects, locations, and the like. Based upon data from the plurality of sensors 103a-103c, the processor 101 may generate a contamination probability value for each element.

The output device 102 may comprise a display (visual, acoustic, haptic, etc.), and the processor 101 may generate indicators of elements of the spatial model having respective contamination probability values exceeding a threshold on the display. The processor 101 may iteratively update the contamination probability value for each element during the medical procedure. The processor 101 may generate a gap value between adjacent elements in the plurality of elements. Also, the processor 101, when one of the adjacent elements is contaminated and the gap value is less than a threshold gap value, indicate the other element also as contaminated.

Another aspect is directed to a method for operating a system 100 for monitoring a sterile field associated with a medical procedure. The method may include operating at least one sensor 103-103c adjacent an area where the medical procedure is to be performed, the at least one sensor for monitoring the area, a patient 105 for the medical procedure, and a medical technician 104 for the medical procedure. The method may include operating a processor 101 coupled to the at least one sensor 103a-103c and for detecting a sterile field event, and an associated location for the sterile field event. The method may further include operating an output device 102 coupled to the processor 101 and for generating an alert indicator when the sterile field event is detected, the alert indicator also including the associated location.

Figure 11:
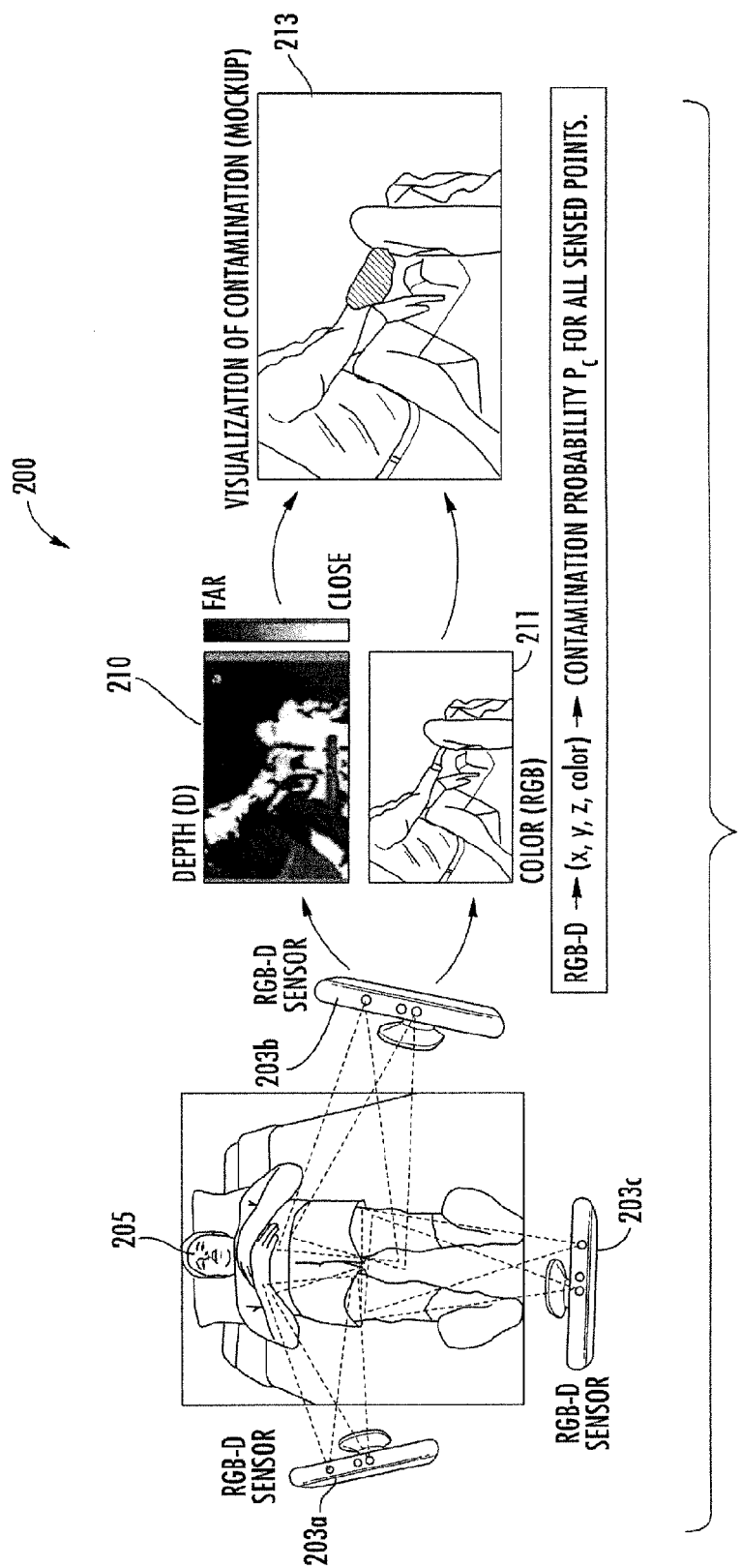
FIG. 11 is a diagram of an additional depiction of the overall proximity/contact detection and visualization concept in another embodiment of the system of FIG. 1.

Referring briefly to FIG. 11, a diagram 200 offers a depiction of an example overall proximity/contact detection and visualization process. In this example, digital cameras and RGB-D sensors 203a-203c (e.g., Microsoft Kinect) measure the three-dimensional (3D) coordinates 210 and colors 211 of points on detectable elements (such as the illustrated surfaces) of the patient 205. Prior surface contamination probabilities combined with stochastic 3D point estimates are used to evolve the contamination probabilities, which are shown to the provider when appropriate, e.g., via a graphical overlay as shown in red in the rightmost image 213.

In the following, with reference to FIGS. 2-11, an exemplary implementation for the system 100 is now described.

1. Introduction

This set of four images 20, 25, 30, 35 depicts a situation where a nurse 38 is training (with a human patient 37 simulator) for a urinary catheter insertion, and the nurse must be trained to avoid contact between sterile and non-sterile surfaces. The faux red (shown here in black and white with outlines) colorizations 32, 36 in the lower images provide an example of how an automatically detected potential contamination might appear in real time using Augmented Reality techniques.

Human contact during healthcare-related activities has an interesting duality: in certain situations it is desirable and even encouraged, while in other situations it is critical to avoid. In a 2011 TED talk, Stanford physician Abraham Verghese spoke about "the power of the human hand to touch, comfort, diagnose, bring about treatment," and how the act of touching in healthcare can become an important ritual for patients even when there is no diagnostic necessity [62].

On the other hand, there are times when touching a patient can have grave consequences. In particular, touching or causing contact with a contaminated object can introduce a healthcare associated infection (HAI). The cost to society and individuals is astounding. By some estimates, HAIs cost society billions of dollars annually. In 2009, economist Douglas Scott found, "Applying two different Consumer Price Index (CPI) adjustments to account for the rate of inflation in hospital resource prices, the overall annual direct medical costs of HAI to U.S. hospitals ranges from $28.4 to $33.8 billion (after adjusting to 2007 dollars using the CPI for all urban consumers) and $35.7 billion to $45 billion (after adjusting to 2007 dollars using the CPI for inpatient hospital services)," and that "the benefits of prevention range from a low of $5.7 to $6.8 billion (20 percent of infections preventable, CPI for all urban consumers) to a high of $25.0 to $31.5 billion (70 percent of infections preventable, CPI for inpatient hospital services)." [27]

On an individual patient basis, HAIs cause discomfort, prolonged hospital stays, and increased morbidity and mortality [52, 56]. According to an article from the Agency for Healthcare Research and Quality (AHRQ) of the U.S. Department of Health and Human Services, there was a five-fold increase in cost and hospital duration, and a six-fold increase in the rate of death for HAIs in 2007:

Adults who developed health care-associated infections (HAIs) due to medical or surgical care while in the hospital in 2007 had to stay an average of 19 days longer than adults who didn't develop an infection, (24 days versus 5 days)" and "For patients with an HAI, the rate of death in the hospital, on average, was 6 times as high as the rate for patients without an HAI (9 percent versus 1.5 percent). Also, on average, the cost of a hospital stay of an adult patient who developed an HAI was about $43,000 more expensive than the stay of a patient without an HAI ($52,096 versus $9,377). [2, 45]

The Center for Disease Control and Prevention (CDC) estimates that during 2011-2012 there were 721,800 HAIs in acute care hospitals in the U.S., including 93,300 urinary tract infections (UTI), 157,500 surgical site infections, and 190,400 for infections of other sites [20]. In 2014 the CDC noted that UTIs are tied with pneumonia as the second most common type of HAI, second only to surgical site infections [52]. A meta-analysis of infection costs and types over 1986-2013 found similar rankings and costs [71]. Among incidents of UTIs, failure to prevent contact related contamination during the catheter insertion is a primary cause of UTI-related HAIs [12, 47, 57]. Some hospitals are now banning nursing students from inserting catheters in patients during clinical rotations. It is now possible for a student to graduate from a nursing program without ever actually having performed this procedure.

The primary defense against such infections is deceptively simple: avoid contact events between any potentially contaminated surfaces and sterile surfaces. Simulation based training has been shown to help [14] but it is very difficult to maintain the sterile field, and to have confidence that you have done so. One has to prepare the area, unpack the catheter kit (FIG. 3, 40), prepare the patient, and perform the procedure on a moving patient. It is relatively easy to violate the sterile field, and not even know it. Worse, the violations can occur through a chain of contacts that can transmit unseen pathogens (e.g., bacteria, viruses, fungi, and parasites) from one surface to another, where the final transmission of the pathogen to the patient happens during what would otherwise seem like a sterile contact. For example, one might unknowingly contact a non-sterile surface with the back of a hand (sterile glove), then scratch that spot using the fingers of the other hand (sterile glove), and then touch the catheter.

Because the infection-causing organisms are invisible to the naked eye, current training and clinical practice of sterile techniques is limited to adherence to "best practices" offered by the CDC and elsewhere [23, 24]. Recommendations include maintenance of sterility, proper insertion technique, and adherence to general infection control principles [13]. These recommendations seem easy, yet studies show that contact incidents resulting in UTIs are common, particularly among new nursing graduates [16]. The most significant aspect of the procedure is not the introduction of the catheter into the urinary meatus, but the ability to maintain sterile technique throughout the procedure. Several general principles govern sterile technique, such as: (1) all items within the sterile field must be sterile; (2) sterile drapes are used to create a sterile field; (3) personnel must never turn their backs on a sterile field; and (4) hands must never pass below the waist [18].

1.1 Current Training Practices

Urinary catheterization skills are typically introduced early in nursing curricula, in a skills laboratory. Students receive didactic content in either a classroom setting or by viewing multimedia tutorials, followed by laboratory expert instruction and practice [63]. At UCF, nursing students receive a brief overview of urinary catheter insertion during the first semester, view a faculty-led demonstration, and may view a skills video. They have one opportunity to practice in lab with faculty supervision, and other opportunities to practice in an unsupervised open lab. In some instances students will offer peer-to-peer feedback. At the end of the semester the students return to the lab for a pass/fail competency validation. The primary reason a student will fail is because of his/her inability to maintain sterile technique.

Gonzalez and Sole [22] recently carried out a study where Baccalaureate nursing students with prior documentation of competency demonstrated performance of urinary catheterization on a task trainer. The procedure was recorded and breaches in technique were identified through review of the digital recordings. Data was available for 13 participants. Participants ranged in age from 21-43 years (mean 26.6). The majority of participants (11; 85%) were right handed. Ten participants (77%) were female and three (23%) were male. The participants' mean self-rating of confidence was 3.6 on a 5-point scale (range 3-5), indicating some confidence in performing the skill. Examination of the video recorded data showed that 10 participants (77%) breached aseptic technique in at least one category, and in some instances several categories.

1.2 Our Vision

The present disclosure envisions automated systems that monitor such sterile procedures during training and practice, looking for risky, proximal, or contact-related events, and providing visual/auditory alerts. The idea is to use sensing and visualization to make potential contamination visible to trainees and practitioners. Some readers might be familiar with the game "Operation" by Hasbro where players use small metal tweezers to remove small plastic objects from openings in a humorously depicted body. Contact with any side of an opening causes the nose of the "patient" to light up and the system to buzz loudly [21]. Anyone who has played that game probably remembers the acute emotional reaction when the buzzer sounds. Similarly we believe that the emotional event of seeing/hearing the virtual transmission of potential pathogens (as it happens, or retrospectively) will instill a more visceral cognitive/muscle memory of the event, resulting in better practices.

Such systems could also be used during actual procedures as an aid to detecting potential contaminations. For example, if the system observing a catheterization procedure detected potentially harmful circumstances, it could offer an alert to the professional, allowing them opportunity to assess the questionable circumstances—from multiple viewpoints, going back and forth in time—and if appropriate they could discard the catheterization kit and start over.

2. This Proposal (Summary, Merit, and Impact)

The present disclosure proposes to develop new methods and systems that monitor trainee/practitioner manipulations during a simulated/real urinary catheter insertion, and provide them with the ability to directly (in situ) perceive the effects of their behavior. Our overall goal is to transform the training and practice of sterile procedures in general, and urinary catheter insertion as a specific example, into a realm of automated oversight with objective visual/auditory indications of performance.

Unobtrusive sensing of proximity/contact between un-instrumented surfaces/objects is a difficult problem. To be effective for aseptic training and practice the approach needs to be comprehensive, accurate, and reliable. Achieving comprehensive sensing is made difficult by observability issues including perspective (visibility with respect to normal contact points and areas), resolution, and sensitivity. The sensing needs to be applied to the relative tracking of all surfaces/objects (people, devices, carts, etc.) in the scene. The surfaces/objects need to be classified in terms of sterility state (e.g., sterile, contaminated, unknown) and any relevant known object or motion characteristics (e.g., expected shape). Probabilities of pathogen transmissions need to be qualified by uncertainties in sensing and object/motion characteristics, and the transmission event chains preserved for training/assessment purposes including visualization and other object/surface state transition detection. New opportunities exist to visualize the sterility state events/transitions using scene/object/surface models and various displays including projectors (Spatial Augmented Reality), see-through head-worn displays (Video Augmented Reality), or fixed displays.

Computer-based systems that make the potential transmission of pathogens visible to humans would transform what is currently a subjective approach to training and practice into an automated process that is objective, controlled, and repeatable. One could incorporate additional virtual content into the visualizations, e.g., depictions of exemplary 3D motion paths. Certain aspects could someday be realized using portable devices, supporting "any time anywhere" training or clinical monitoring. While the present disclosure focused on urinary catheterizations as a concrete example, the methods could apply to other procedures with similar isolation requirements, e.g., intravascular catheterizations, the handling of biological samples, or radioactive materials. The teachings of the present disclosure may be applied to clinical or laboratory-based practice—alerting practitioners about potential breaches during procedures, affording the opportunity to discard the materials and start again.

3. Research and Related Activities

As shown in flowchart 45, there are six primary aspects of our research and related activities, described in Sections 3.1-3.6 below. The diagram depicts the functional relationships. The large dashed-line box indicates a testbed system (Section 3.4) comprising the three continuous processes (circular arrows) described in Sections 3.1-3.3. The testbed will be used for testing and evaluation (Section 3.5), and activities aimed at broadening our impact (Section 3.6). A project timeline is discussed in Section 3.7. (Blocks 46-48).

3.1 Surface/Object Detection and Tracking

To facilitate the determination and propagation of contamination status, the present disclosure can detect proximity and contact conditions within the scene by tracking various spatial elements (e.g., objects, surfaces, etc.), estimating the inter-surface "gaps," and the likelihood of pathogen transmission. To this end, the present disclosure must identify the location of such elements and track their movements throughout the environment. One can evaluate the effectiveness of different sensors and sensor configurations from both "first-person" and "third-person" perspectives.

Ideally the system would support unencumbered tracking and contamination estimation, free of tracking markers or other electronic devices, however we do not exclude the use of such tracking markers or other electronic devices.

In general the sterile environment tends to be quite well defined, having a relatively consistent, finite list of expected objects; likewise, actions that typically occur are limited. Humans and certain objects serve as easily identifiable, a priori known scene elements; even partial recognition provides additional information about surfaces that are not visible. In particular, one would desire comprehensive detection and contact assessment for four major classes of elements that may appear in the scene.

(i) Humans: both the patient and trainee are of paramount importance, as they are the primary means of initiating motion. While the patient is mostly (though not always) static, and considering only the lower body may be necessary, the trainee is expected to move; one can account for the body as a whole—the torso, head, arms, elbows, legs, and so on. Human hands, including fingertips, are well-defined and likely points of contact, so one may focus on them independently of the whole body. (ii) Recognizable three-dimensional objects: these are objects in the scene for which we can estimate bounding volumes. Where possible, one can track such objects as they move throughout the scene. Example objects include the catheter (critical), the bed, and bedside table. One can model the sterile drape and the clothing of the trainee and patient using cloth modeling techniques to allow for recognition. (iii) Segmented surfaces: for some surfaces, one may be able to perform rudimentary recognition, but bounding volumes are not available. Additional information such as object extents will likely not be available for surfaces in this category. Cloth surfaces, such as the sterile drape and clothing, may be categorized as segmented surfaces if they cannot be otherwise modeled. (iv) Unrecognizable objects and surfaces: the remaining objects for which recognition might prove difficult, due to size, appearance, or other qualities. While we can detect the presence of such surfaces, one cannot have access to additional information. However, it is important to note that such objects will play a role in the propagation of contamination status throughout the scene. Examples include hair, a lanyard/tie, and jewelry—although some of those might be modeled.

Figure 5:
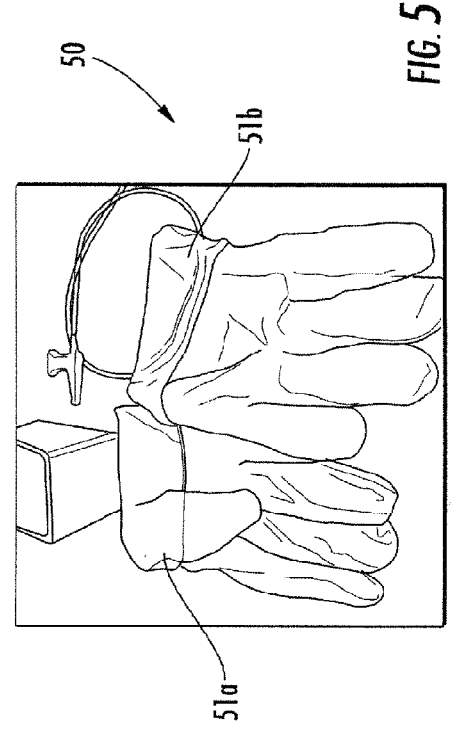
FIG. 5 is an image of gloves in the sterile field, according to the present disclosure.
Figure 9:
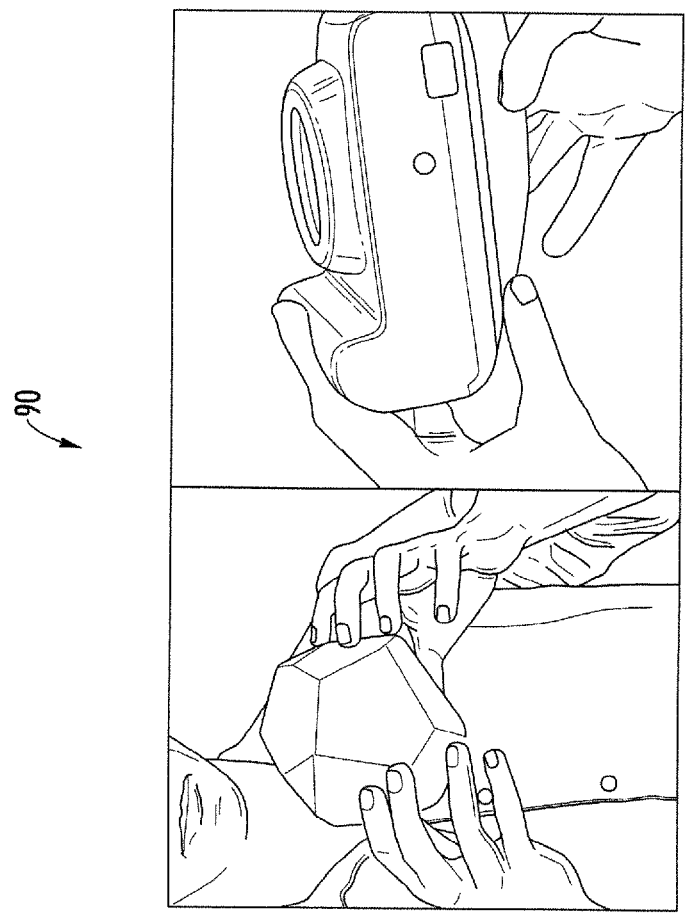
FIGS. 8-9 are images of components in the system of FIG. 1.
Figure 8:
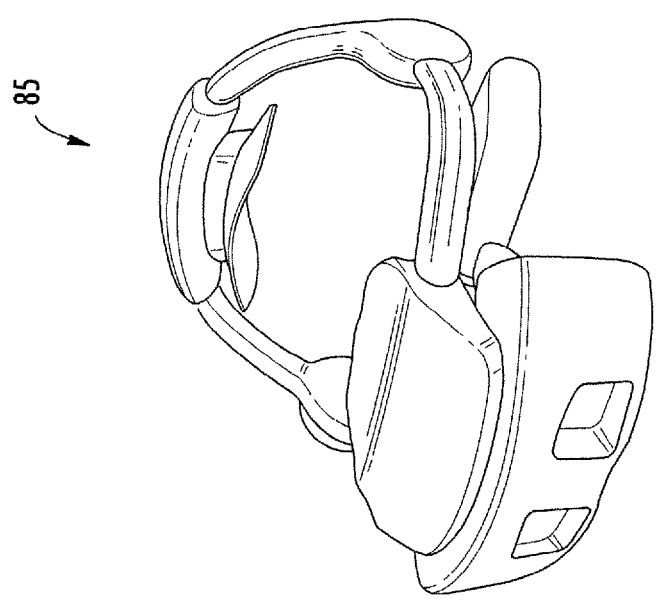
Figure 10:
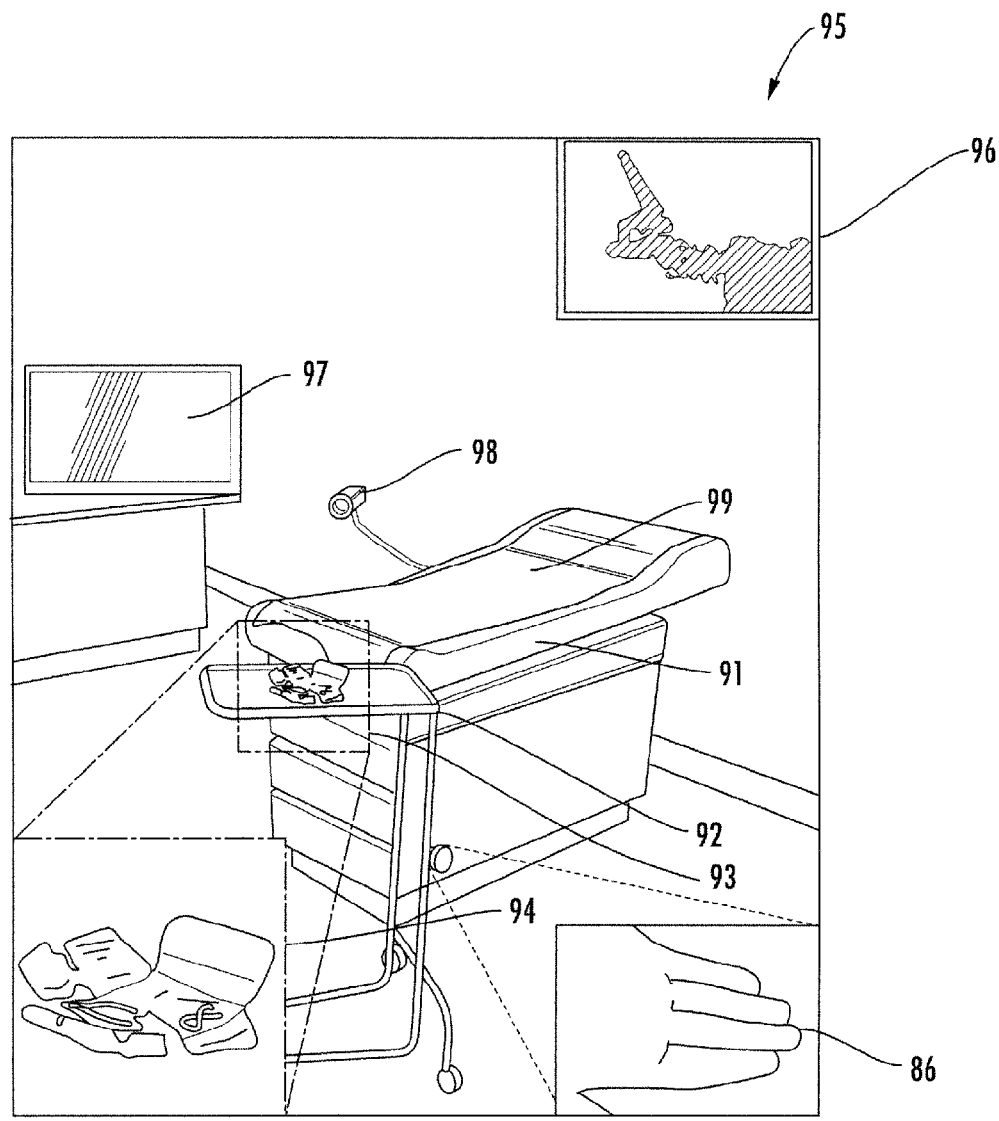
FIG. 10 is an image of another embodiment of the system of FIG. 1.

One can leverage opportunities to inject signal into the scene to facilitate detection in ways that do not adversely affect the trainer, trainee, or patient. For example, the latex gloves included in the catheter kit are sterile on their outside surface, and non-sterile on the inside. As shipped, the gloves have an approximately 1-2 cm band 51a-51b rolled back (turned "inside-out") at the opening (FIG. 5, 50). That band is the part to be handled with a non-gloved (presumed clean, not sterile) bare hand when donning the first glove. Once the first glove is donned, it can be used to help don the second glove (because its exterior is sterile). Normally this non-sterile inside-out interior portion of the glove would be very difficult to distinguish visually from the sterile exterior of the glove, as they are the same color. However we believe we could obtain or make gloves that are red (for example) on the inside and green on the outside (sterile) such that the non-sterile rolled back band will be more clearly identifiable to the system, and more distinguishable from human fingers. Similarly one can add color or known fiduciaries to the bedside table or other props.

3.1.1 Sensors

In general, detecting the contact/proximity of hands, fingers, or other objects with surfaces can be handled in a variety of ways. One could employ electronic sensing approaches using capacitive sensors, electronic meshes, or other kinds of sensors [17, 25, 55]. However to maximize the chance for later adoption by others we prefer (though do not require) the use of unobtrusive commercial-off-the-shelf components, and to minimize the use of specialized modifications. As such we are focusing on red-green-blue and depth (RGB-D) devices (such as Kinect (as available from the Microsoft Corporation of Redmond, Wash.), Leap Motion (as available from Leap Motion, Inc. of San Francisco, Calif.), or other similar sensors) and camera imagery (visual or infrared). RGB-D sensors allow for the simultaneous capture of both color imagery and depth information and are also capable of providing additional information, such as skeleton tracking. Our approach is to employ a carefully arranged sequence of multiple RGB-D sensors for the purpose of contamination detection (Section 3.2). The depth information sensed by each sensor can be combined to allow us to reason about the scene as a whole. Infrared cameras may capture information that aids in the detection of human body parts. While sensing a surface itself yields important information about the environment, the behavior of "gaps" between surfaces also offers valuable information. A gap would normally give rise to depth discontinuities along the depth/image sensor rays; as the gap disappears a closer surface will appear (arising from the contact) along the same rays. As such, contact can be sensed in 3D by observing the presence/absence of gaps.

3.1.2 Sensor Placement

In general, the choice and placement of sensors in a sterile technique training system is critical in terms of the need for visibility and observability conditions affecting the estimation of inter-surface proximity and contact conditions. However, one needs to consider the cost and potentially encumbering nature of the sensors, as well as the growth in complexity of the system of sensors as a whole. While one would not want to over-constrain the design of a sterile technique monitoring system, one would like to avoid adding more sensors than are needed for the volume. As such, first-person sensors could be limited to a pair of miniature cameras configured as stereo, and if needed an RGB-D sensor. Third-person sensors could include visible/infrared (IR)/RGB-D sensors. One can evaluate candidate sensor configurations in at least two ways. First one can leverage prior sensor optimization work, e.g., [3,4,69], and perform an asymptotic localization uncertainty analysis for each candidate design, including cases with expected occluders (hands, etc.). One can also employ time-motion analysis through a series of simulations to generate a training dataset to further optimize for exemplary scenarios.

3.1.3 Methods

The question of "what touched what?" in a dynamic environment requires essentially solving at least the following problems: (i) sensor information fusion for more reliable and more accurate analysis and detection, (ii) tracking of objects and sensors and their dynamic configuration, (iii) recovering the relative geometry of the scene as it evolves and determining conditions of interest, i.e. proximity or contacts between objects, (iv) updating contamination states of surfaces and objects, and estimation and propagation of probabilities over time and space.

Sensor Fusion: A crucial step in sensor fusion is the alignment and registration between sensors [10], and the ability to deal with reconfiguration of a dynamic network of sensors [35,36]. Individual raw point-clouds from different sensors can be aligned using either image-domain features (such as SIFT, HoG, STIP, etc.), or 3D features such as the ones that we proposed in [15] based on the eigenvectors of structure tensors. The space-time alignment allows for fusing of information across multiple sensors, including in particular first-person viewpoints. In previous research projects we have developed methods for dynamic networks of cameras for surveillance [5, 28-30, 33-39]. While that work provides a strong heritage to this disclosure, there are discernible differences that make this disclosure of particular interest, e.g. multiple sensor modalities (depth/IR/visible), and the fusion of first-person perspectives with third-person perspectives. For example, when employed together, multiple RGB-D sensors experience crosstalk, as each device projects its own structured light patterns over its field of view; Butler et al. [9] and Maimone and Fuchs [46] independently developed a simple hardware solution to remove such interference via gentle vibrations of the sensors. The fusion of information provided by multiple RGB-D sensors will allow for the recovery of depth and color/IR information throughout the scene. As the number of sensors viewing a particular object increases, the certainty about the object's size and position increases.

Tracking and Sensor Reconfiguration: Recently we studied the problem of dynamic scene modeling and selective subtraction as an extension to the classical background subtraction methods from a third-person perspective [7,40]. One can extend this to multiple sensors to allow for the segmentation of the dynamic scene into objects of interest, separating them from the static background, while taking advantage of depth and IR information. Recently, first-person viewpoint segmentation methods [26, 49] have also gained growing interest due to devices such as Google Glass and Head-Worn Displays. Such first-person methods can also be extended to multi-sensor dynamic settings. To deal with multiple sensor configuration and dynamics (sensors' pose, location, and calibration dynamics) our methods in [5, 33-36] can be extended to take into account additional constraints introduced by other sensing modalities such as depth and IR. In particular, unlike our earlier work where the geometry of the scene was unknown, one can use depth features and discontinuities as additional constraints. Furthermore, the specific problem that we face has inherent geometric constraints in terms of time-space localization and motion, which can be exploited to counter the additional degrees of freedom that first-person perspectives introduce in the problem.

Recovering Relative Geometry and Contacts: Finding where and when the contacts happen between surfaces and objects is a core challenge related to this disclosure. Once can tackle this challenging problem from multiple directions. A single RGB-D sensor provides a two-dimensional matrix of depth values over its field of view. The manner in which this two-dimensional matrix changes over time provides information that can be used to detect proximity/contact, which can also be observed as the disappearance of "gaps" between known objects. For instance, as a human hand approaches a table, the gap of space separating them becomes smaller and smaller, eventually disappearing when the contact occurs: hence, the closing of a gap indicates that contact is likely to occur. One advantage of modeling conditions in this fashion is that the depth at which a gap disappearance occurs can be used to localize a contact event.

Figure 12:
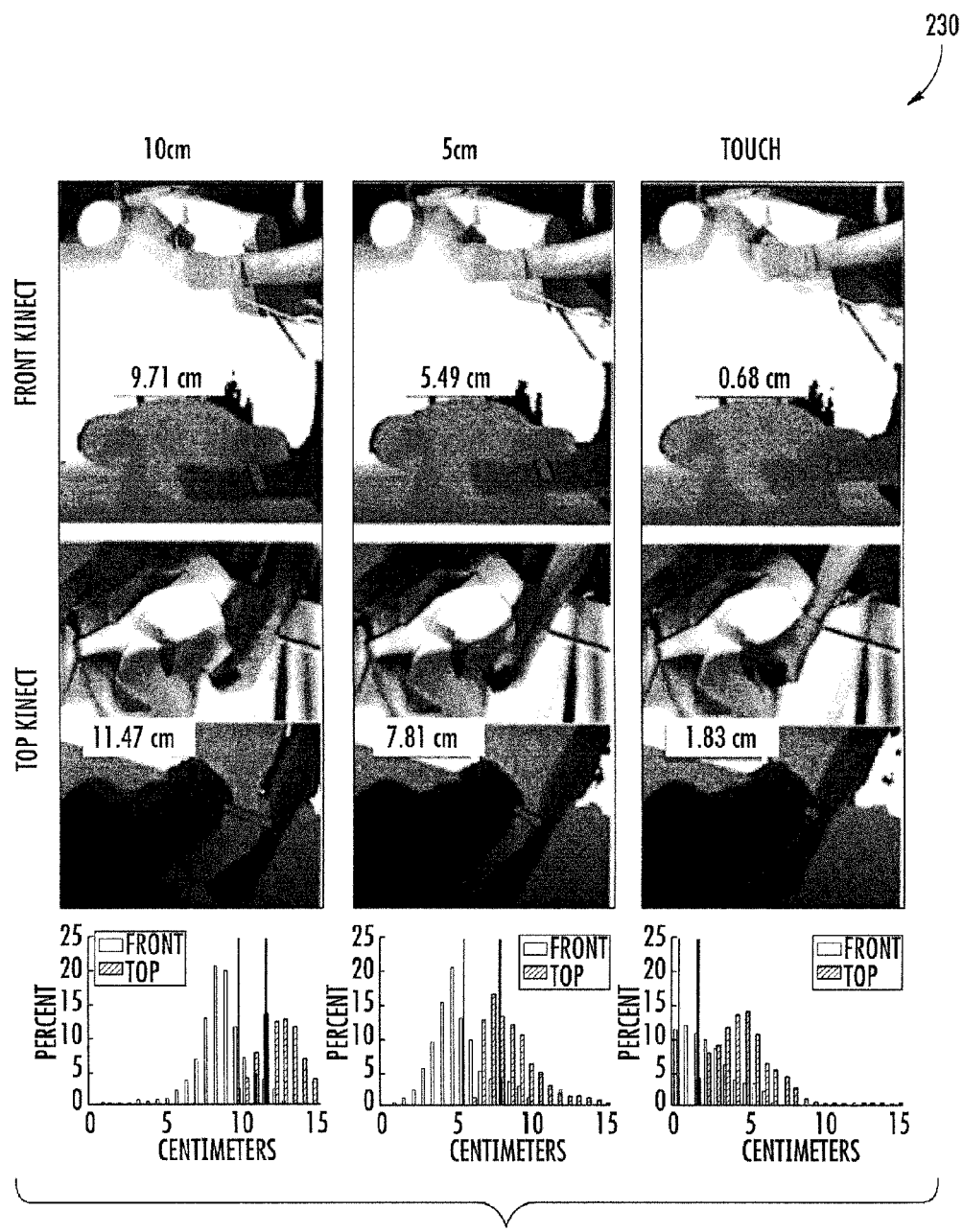
FIG. 12 is a diagram of examples of depth and color imagery from a top and front-mounted sensors at three different gap distances in another embodiment of the system of FIG. 1.

FIG. 12 is a diagram 230 an example of such gaps. Front and top Kinect data for known distances of 10 cm, 5 cm, and 0 cm. First row: color and depth images from a front Kinect. Estimated distances account for the thickness of the user's wrist, approximately 5 cm. In the lower-right of the color images one can see the catheter and the graduated measurement rod. Second row: color and depth images from a top Kinect. In both we illustrate (with a blue line) a single inter-surface distance selected from the measured samples. Third row: histograms of a dense set of shortest distances between the user's arm and the task trainer, from the front and top perspectives. The blue and red dotted vertical lines reflect the distances indicated in the first (front) and second (top) rows above.

Different scene elements require various detection mechanisms. For example, human detection can make use of human body models to constrain depth values such as from the RGB-D sensor [53, 67]. Beyond the skeletal configuration, we are really interested in the shape of the body, as it is the surfaces that will contact other objects. One can use generic or custom deformable body models from the RGB-D sensor, e.g., as in [1, 11, 31, 60, 65]. However, such methods are concerned only with the contact of fingertips on planar surfaces; for the purposes of this disclosure, one must detect touch across a variety of nonplanar objects, including the backs of hands.

To solve the problem for an arbitrary surface shape, one can model it in a piecewise planar fashion, e.g., using a Delaunay triangulation. Any two or more cameras in the network of sensors, including potentially a pair of body-mounted miniature cameras in the case of a first-person perspective, can then be used to determine gaps and contacts and the associated probability distributions. The solution is inspired by our work in [6], where we demonstrated that projective depth of a set of arbitrarily moving points in 3D space with respect to a reference plane can be used to determine their relative distance from the plane. The same approach can be used to determine how close a set of moving points are to a surface patch defined by a triangle.

In particular, let $m_i$ and $m_i'$ be a set of corresponding object points viewed in two cameras at a given instance t in time, and let H be the homography induced by a surface patch between the two views. One can define the probability $$Pr(g) \propto Pr(\rho i) = 1 - \frac{\partial \rho i}{\partial t} \bigg/ \left\|\frac{\partial \rho i}{\partial t}\right\|, \text{ where } \rho i = \frac{m_i' - Hm_i}{e' - Hm_i}. \quad (1)$$

e' is the epipole in the second camera (i.e. the image of the first camera center in the second camera view), and $$\frac{\partial \rho i}{\partial t} \bigg/ \left\|\frac{\partial \rho i}{\partial t}\right\|$$

is an element of the characteristic vector as defined in [6], which is invariant to camera pose and parameters. FIGS. 6A-7B illustrate the basic idea of estimating the dynamically evolving probabilities of gaps using the components of the characteristic vectors over time. In these diagrams 60, 65, 70, 75, 80, the gap for four different body points (right elbow 78, 83, left elbow 77, 82, right hand 79, 84, left hand 76, 81) are measured relative to the plane defined by the actor's neutral body pose that we called the canonical pose. In practice, using this approach, one can measure the distance of any set of moving points (e.g., hands, instruments, etc.) to any plane in the scene (e.g., patches of a surface).

Diagrams 60, 65, 70, 75, 80 show how elements of characteristic vector [6] characterize the gap (distance) between various body parts and a person's body. Note that viewpoint and camera parameters do not affect these measures (projective invariance property). In a similar manner, the distance of object or body points to any surface patch can be measured using this approach. (Note: the colored hand and elbow markers were added to the images for clarity—they are not part of the scene.)

In general, we expect that one would need to take into account object dimensions and scales by making use of the segmentation as described above to define envelopes around objects and also take into account anthropometric constraints. One would express the likelihood of contamination of scene elements in terms of the probability distributions. Assuming local conditional dependency for $Pr_{(Pi)}$, the joint probability distributions of gaps can be locally represented by probability distributions in a Bayesian network to determine the probability $P_{g<\epsilon}$ that a gap is less than some nominal tolerance $\epsilon$. Such probabilities can then be used to model the contamination probabilities and hence the propagation of such contamination, as described in section 3.2.

Finally, Kinect Fusion [51], augmented by the work of Karpathy et al. [42], offers another solution, by providing a mechanism for mapping and tracking arbitrary scenes using depth information from multiple Kinect devices. Karpathy et al. [42] illustrate a method for discovering objects within a three-dimensional scene found via Kinect Fusion using measures of "objectness." For recognizable three-dimensional objects that can be modeled in advance—e.g., the catheterization kit, catheter, sterile wipes, bed, or table—one could modify this objectness score to consider known object properties.

Updating Contamination States: As a means of updating contamination states, one can maintain historic information about the spatial state, including positions and coordinate frames, of each element present in the scene. Spatio-temporal tracking can allow for the prediction of their motion. Each element class could be described by different structural and process models. Tracking human elements could utilize articulated body joint-based models. Rigid body models with fixed extents more appropriately model recognizable three-dimensional objects. For segmented surfaces and unrecognizable objects and surfaces, which are likely to be non-rigid, one could employ deformable models and cloth models. Moreover, one can account for the distinct types of motion these elements may exhibit, i.e. different process models; in particular, human motion is expected to have more energy (move more) than other elements in the scene. One can make the tracking volume larger than the sterile volume such that items leaving the sterile volume can be automatically marked as contaminated, per the normal practices of sterile technique. If objects exit the tracking volume they will cease to be updated; if they re-enter they will be treated as new items. (This also matches the spirit of current sterile technique practices.) Human detection and tracking can be performed with stereo or multiple-view camera configurations [43, 48, 70] or with a depth camera such as the Kinect [67]. For on-line estimation of the pose of objects, one can explore the use of stochastic filters, such as the Kalman filter [8, 32, 41, 66] or particle filters.

3.2 Contamination Determination/Propagation

The development of mechanisms for probabilistically estimating the evolving contamination states of all surfaces (or surface patches) in the scene is one of the primary challenges. An underlying principle of our approach is that each element of the spatial model (e.g., surface or surface patch) has an associated contamination probability Pc. All such elements would be considered contaminated ($P_c=1$) unless explicitly denoted sterile ($P_c=0$). Elements that are known to be sterile would automatically and/or manually be identified by the system or trainer/teacher. During ongoing use, the system would iteratively re-evaluate the contamination probability Pc for each (and every) element in the scene, based on the probability of contamination by every other such element. When the "gap" g between two surfaces is estimated to be less than an a priori tolerance $\epsilon$, the contamination probability $P_c$ of one element can be transferred to the other, although neither can be contaminated more than the maximum of the pair. Because the "$g<\epsilon$" and "prior contamination" events are independent, it should be possible to compute the degree of potential cross contamination as the product of the two probabilities.

More specifically, we assume one can have (per Section 3.1) a dynamic pose x, pose error covariance E, and model structure M for most scene elements, to assist in real-time inter-element contact detection ($g<\epsilon$). While contact detection for rigid bodies could leverage the well-investigated body of literature on collision detection, deformable objects such as catheter tubes and sterile drapes, as well as noisy point clouds, present challenges. To accommodate deformable and pliant surfaces (e.g., catheter tubes and sterile drapes) one can explore the use of bounding volume hierarchies (BVH). A BVH is an efficient data structure for collision detection, and generally involves fitting the smallest geometric primitive to encompass a region of interest. While convex hulls may offer a fairly tight fit for a BV, one may be able to further improve the accuracy of the contact detection (and hence, contamination determination) using techniques such as gradient vector flow active contours [68].

Given the BVH of the scene, we would first prune the elements in the scene to identify all candidate pairs A and B between which contact may occur. We would do so accounting for the stochastic nature of the BVH data [54,59]. We would then compute the contamination probabilities between all such pairs. Leveraging the information from the tracking method outlined in Section 3.1, we assume each element in the scene has an estimated pose x, pose error covariance E, and model structure M defining (or a function of) the BVH. The pose and error covariance together describe the first two statistical moments of the element, and can be represented as $X=(x, \Sigma)$ for each scene element X. One can define a function F that transforms all points M of this scene element X (e.g., surface/patch/vertices) into a common coordinate frame (for instance, from the object coordinate frame to world co-ordinate frame) by taking into account the statistical moments (poses and uncertainties) and the model structure.

$$M'=F(X,M) \quad (2)$$

For a candidate pair of potentially contaminated surfaces (patches) XA and XB in the scene, one can then estimate the gap using the transforms M0A and M0B computed from Equation (2). Correspondingly, a function "gap" will return the minimum Euclidean distance between all point pairs M0A and M0B as a tuple G of two scalar quantities gμ and gv which represent the mean and variance of that minimum scalar distance respectively (Equation 3).

$$G=[g_\mu,g_v]=\text{gap}(M'_A,M'_B) \quad (3)$$

One can then represent the separation or "gap" between all vertices of the pair of elements defined by $X_A=(x,\Sigma A)$ with $M_A$, and $X_3=(x_B, \Sigma B)$ with $M_B$. The gap can be modeled as a normal distribution with the probability density function (pdf) $p_g$ centered about mean $g_\mu$ with variance $g_v$, as in Equation (4).

$$p_g(x, g_\mu, g_\upsilon) = \frac{1}{g_\upsilon \sqrt{2\pi}} \exp\left(-\frac{(x-g_\mu)^2}{2(g_\upsilon)^2}\right) \quad (4)$$

Discrete Contact Probability Estimation. Given this pdf $p_g$, we can compute the probability of the gap between the pair of elements being less than some tolerance $\epsilon$, i.e.

$$P_{g<\epsilon} = \int_{-\epsilon/2}^{+\epsilon/2} p_g(x, g_\mu, g_\upsilon) dx. \quad (5)$$

After selecting all candidate pairs (A, B) via a careful process of screening (e.g., leveraging their stochastic bounding volume hierarchies), for each pair one can update the new contamination probabilities as follows:

$$P_c^{A^+} = \max(P_c^A, P_c^B | P_{g<\epsilon}).$$

$$P_c^{B^+} = \max(P_c^B, P_c^A | P_{g<\epsilon}). \quad (6,7)$$

I.e. the probabilities $P_c^A$ c and $P_c^B$ c can be updated to posterior values that are the maximum of the contamination probability prior to the test and the probability in light of the potential contact. By iteratively repeating this process for each set of candidate pairs in the scene, probabilistic estimates of the contamination for each element can be maintained over time.

Continuous Proximity Estimation. We also envision expanding with a continuous proximity feedback paradigm. In this mode the system would compute the $P_c$ as described in Section 3.2, however it would not replace the previous value in Equation (7). Instead it would always/only compute the maximum $P_c$ over the elements, at every moment. Hence elements of the scene, in this special mode, never truly become "contaminated" any more than when they started, but a trainee, for example, would be able to tell as the risk of contamination increased, and then back away, e.g., retract their hands from the danger point. In this way, as the trainee moves their hands/objects around the environment, the maximum dynamic Pc signal (per element surface/patch) will rise and fall in correlation to the proximity to non-sterile objects.

3.3 Interactive Visualization/Feedback (In Situ, Real Time)

While estimating the contamination probabilities Pc throughout the scene is necessary (Sections 3.1-3.2 above) it's not sufficient to achieve our envisioned system. Visualizing the dynamic estimated contamination states is a critical component, as is the user interface to control the visualization and the overall system behavior. One could employ several approaches. For example, one could employ a video-based Augmented Reality paradigm using a fixed display near the subject (no head worn displays). One could choose one of the camera views (perhaps allow the user to choose) and overlay that live video feed with the dynamic scalar contamination probabilities Pc throughout the scene, for example with a varying opacity or particle motion. See FIGS. 2A-3 for mockups of augmented live video.

For first-person visual feedback, one can use a Canon MR Platform HMA1 "Mixed Reality" Head-Worn Display system (FIGS. 8-9, 85, 90) or similar and overlay the visual feedback onto the per-eye camera imagery. One can similarly use the Oculus Rift DK2 (high definition resolution, low latency tracking and reduced motion blur) with a suitable Augmented Reality kit to test this paradigm. One can also augment the visual feedback with continuous or discrete audio feedback (see below).

One can display feedback for both discrete contact events and continuous proximity conditions. For discrete contact events one could display the overlay (Head-Worn Display, fixed display, or projected imagery) in 100% opacity at the moment "contact" (below the $\epsilon$ threshold) was determined. To convey more continuous feedback one can start with simply varying the opacity of the overlay depending on the proximity or evolving contamination probabilities, e.g., $P_c^{A+}$ and $P_c^{B+}$ c above. One can also employ more sophisticated visualization techniques [64] and visualization toolkits [44, 58]. Finally one can employ audio signals correlated with contact or risky conditions, e.g., a beep on contact, or higher risk behavior→higher pitch. We believe that these continuous paradigms will help trainees develop "muscle memory" related to the safe regions and behaviors within the sterile space.

To support assessment one can also develop a user interface with multiple features already requested by the Nursing faculty who train subjects in sterile technique at our institution. For example the user interface needs to support the specification of various system parameters, such as the e value from Equation (5) in Section 3.2. The trainers would like to have semi-supervised behavior—that is, students can practice alone, and the faculty can monitor their skill level remotely. The system would support tracking the performance over time, perhaps being notified if the performance is poor. Each student would be assigned an ID number, and their overall performance (duration, breaches, speed, etc.) would be logged. The trainers could be given the option to perform the monitoring remotely.

3.4 Testbed

To evaluate the proposed approach, one can build a hardware-software prototype sterile technique training testbed, such as we are doing. As indicated in the illustrative image 95, our test bed 99 will replicate the real setup as much as possible—e.g., a real exam table, bedside table, etc. The image 95 illustratively includes a depth data view 96 from the image sensor, an example IR camera image 86, a zoomed in illustration of the trainee kit with sterile elements 94, and a box noting the sterile field 93.

Multiple sensors 98, 91 (e.g. Kinect, IR) can be appropriately placed in the scene (see Section 3.1) to maximize observability in the sterile region, e.g. to detect/track hands, probabilistically estimate "gaps" between surfaces. To support further performance evaluation, one can stage a prototype sterile technique training testbed within a large existing tracking infrastructure space, for example, one that consists of Vicon and NaturalPoint cameras. These can be leveraged to monitor activities outside the sterile zone. One can also use eye tracking, physiological sensing, and other sensing in that space.

This illustrative embodiment includes a display 97 for feedback and review, sensors 98, 91 coupled to the processor, and an instrument tray 92.

The algorithms developed can be implemented on a multi-threaded system that interfaces with all sensors observing the sterile zone. In addition, this data can be synchronized with the data from external tracking infrastructure using VRPN protocols [61] or the like. One can also be recording video and audio activity in the entire scene during the process (standard IRB protocols will be followed). One can ensure synchronization between the sensor-based sterile-training data and the audio/visual data in the entire scene (to support review/analysis). In order to provide a trainee with feedback (both real-time and offline) during the process, the system may include a display setup in a non-intrusive location. This could be a touch-enabled surface that allows a trainee to scroll through and view events during the training session.

3.5 Experimental Evaluation

In Section 1 we outlined the way in which students in the UCF Nursing program are trained on sterile technique. Here we describe plans to carry out human subject experiments to help assess our prototype sterile technique training testbed, including the effectiveness of adding it to conventional training. In general, the experiment will be carried out as part of a proposed sponsored research project. In particular the experiment will be carried out during three experimental periods beginning at the end of Year 1 of the project. Experimental Period 1 (EXP-1) will involve a series of small formative experiments to assess the various visualization and user interface options. EXP-2 will involve initial training and assessment in two groups: a Control group using traditional training methods, and an Intervention group supplementing the traditional training with use of our prototype sterile technique training testbed. Ensuring that all of the students receive the same didactic and faculty demonstrations, some form of training with a mannequin and real devices, and be assessed via the normal faculty observation mechanism, will help reduce risk. EXP-3 (the subsequent semester) will re-assess the skills two or more times to look at the perishability of the learned skills.

EXP-1: Visualization and User Interface—Formative Evaluations. During this period, we will carry out a series of small formative experiments, with Nursing faculty and students (not involved in EXP-2 or EXP-3 below) as subjects, to assess the various visualization and user interface options. For example one can compare a Head-Worn Display interface that supports direct overlays of the risk, contamination, etc. in the visual field with a nearby fixed display that shows a video overlay on an adjacent fixed display. (See Section 3.3.) We also plan some "focus group" gatherings with faculty and students (nursing and computer science) to discuss interface options and get feedback/ideas. Specifically with the instructors one can explore various interface elements related to specifying thresholds, forms of data collection, and automated analysis.

EXP-2: Training of Sterile Technique Skills Initial training and assessment will be carried out in two groups: a Control group using traditional training methods, and an Intervention group supplementing the traditional training with use of our prototype sterile technique training testbed. Participants: UCF College of Nursing B.S. nursing students. There will be approximately 120 students in the cohort. Setting: The experiments will take place in our laboratory at UCF's Institute for Simulation & Training, which is where the prototype sterile technique training testbed will be developed. There we also have available head tracking and other subject monitoring equipment. We can cordon off a training space where we can set up both a traditional task training station, and our prototype sterile technique training testbed. We could potentially test both conditions in the same space, simply not using the automated capabilities in the Control Group. (This would expose the Control Group to the sensors and associated mechanical infrastructure, which might be good so that any effects associated with the presence of that equipment is common to both groups.) Hypothesis: Students who practice urinary catheter insertion skills using our prototype sterile technique training testbed (with immediate and timely feedback relative to breaches in sterile technique) will be more competent in performing the procedure at the end of the semester during final testing. Experimental Design: Students will be randomized into two groups (Control and Intervention). Both groups will receive the overview, didactic, and faculty led demonstrations. The Control Group will practice on the traditional task trainer on the day of instruction, and then again on five subsequent dates during the semester (15 week semester). Practice will be consistent with usual practices—an open lab with students "supervising" each other, with video and reference materials made available. The Intervention Group will practice on our prototype sterile technique training testbed on the day of instruction, and then again on five subsequent dates during the semester. Practice will be consistent with established norms—an open lab with students supervising each other and practicing on the prototype sterile technique training testbed. Dependent Measures: Data to consider collecting after the semester is complete and before final testing will include (1) General confidence, (2) Self-efficacy, (3) Perception of mastery, (4) Ease of use, (5) General perception of the task trainer, and (6) Perceived value of the task trainer. Finally we will employ the quantitative dependent measures described below. Pilot: The full EXP-2 evaluation of the prototype sterile technique training testbed will be preceded by a pilot to test our study design and protocols.

EXP-3: Retention of Sterile Technique Skills Students from both groups will return the subsequent semester at two or more prescribed times—not too soon after the start of the semester. We will assess the retention level and decay rate of the psychomotor skills in each group. Participants: The same as EXP-2. Setting: The same as EXP-2. Hypothesis: Students in the Intervention Group (those who use our prototype sterile technique training testbed) will have enhanced skill retention vs. the Control Group. Experimental Design: At the prescribed times, students will be given a new unopened catheter kit and asked to perform the procedure. In order to ensure familiarity with packaging and supplies, the kit will be identical to those used during the prior practice and demonstration. Students will be allotted 15 minutes to perform the procedure. Faculty will provide feedback after the procedure is completed. Participants will be debriefed after the procedure. Dependent Measures: The same as EXP-2.

Common to EXP-2 and EXP-3 Independent of this proposed effort we are developing systems to automatically record and analyze behavior of human subjects during experiments. The system supports synchronized logging of video, speech, and subject head tracking using our Vicon tracking system. One can also adapt the system to log the dynamic scene object/surface pose state (Section 3.1) and contamination state determination/propagation (Section 3.2). One can develop computational methods to process this data into quantitative metrics such as reactions to contact event notifications, stability of motion, and efficiency of motion (as an indicator of confidence).

3.6 Outreach—Broadening Our Impact

As part of our proposed sponsored research project, our computer science (CS) and nursing students will work together to co-develop specific interaction paradigms. We also plan to submit a proposal for a CS "senior project" related to the project, attempting to engage (partner) additional CS and nursing students. This is all part of a larger effort to help foster a culture of cross-discipline thinking. More broadly we plan research relevant public demonstrations extended to local primary school students and community citizens, where we share our systems/results with the aim of inspiring the next generations of nurses, doctors, scientists and engineers. We expect that many (children in particular) will appreciate an "Operation" demonstration, where the system buzzes if you violate the sterile technique. If our hypotheses about improved outcomes when using our testbed are supported by our human subject experiments (Section 3.5), we will provide access to the testbed on a more permanent basis via the UCF nursing curriculum to both improve training and obtain further experimental data. Beyond our lab-based testbed, we plan to investigate a laptop-based prototype that could be used by trainees more frequently on their own. This would, for example, support more/repeated training of the unpacking of the sterile catheter kit, which is relatively difficult to do, but among the most well defined parts of the procedure. Our approach has the potential to be the "new normal" for training in a sterile environment. Finally, we have a growing relationship with Florida Hospital, and they have a keen interest in reducing the rate of UTIs. They are partnering with us on a planned complementary NIH proposal to examine the most frequent sterile field breaches during urinary catheter insertions, and we expect to engage the same researchers in this effort.

REFERENCES the contents of each reference are hereby incorporated by reference in their entirety

[1] A. Agarwal, S. Izadi, M. Chandraker, and A. Blake. High precision multi-touch sensing on surfaces using overhead cameras. In Horizontal Interactive Human-Computer Systems, 2007. TABLETOP '07. Second Annual IEEE International Workshop on, pages 197-200, 2007.

[2] AHRQ. Health care-associated infections greatly increase the length and cost of hospital stays. In AHRQ News and Numbers. Agency for Healthcare Research and Quality (AHRQ), U.S. Department of Health and Human Services, Aug. 25, 2010.

[3] B. Danette Allen and Greg Welch. A general method for comparing the expected performance of tracking and motion capture systems. In VRST '05: Proceedings of the ACM symposium on Virtual reality software and technology, pages 201-210, New York, N.Y., USA, 2005. ACM.

[4] Bonnie Danette Allen. Hardware Design Optimization for Human Motion Tracking Systems. Ph.d. dissertation, The University of North Carolina at Chapel Hill, Department of Computer Science, Chapel Hill, N.C., USA, November 2007.

[5] Nazim Ashraf and Hassan Foroosh. Robust auto-calibration of a ptz camera with nonoverlapping fov. Proc. of IAPR International Conference on Pattern Recognition (ICPR), 2008.

[6] Nazim Ashraf, Chuan Sun, and Hassan Foroosh. View-invariant action recognition using projective depth. Journal of Computer Vision and Image Understanding (CVIU), 123:41-52, 2014.

[7] Adeel Bhutta, Imran Junejo, and Hassan Foroosh. Selective subtraction when the scene cannot be learned. Proc. IEEE International Conference on Image Processing (ICIP), 2011.

[8] Robert Grover Brown and Patrick Y. C. Hwang. Introduction to Random Signals and Applied Kalman Filtering: with MATLAB Exercises and Solutions. Wiley & Sons, Inc., third edition, 1996.

[9] D Alex Butler, Shahram Izadi, Otmar Hilliges, David Molyneaux, Steve Hodges, and David Kim. Shake'n'sense: reducing interference for overlapping structured light depth cameras. In Proceedings of the 2012 ACM annual conference on Human Factors in Computing Systems, pages 1933-1936. ACM, 2012.

[10] Xiaochun Cao, Jiangjian Xiao, and Hassan Foroosh. Camera motion quantification and alignment. Proceedings of IAPR International Conference on Pattern Recognition (ICPR), 2:13-16, 2006.

[11] James Charles and Mark Everingham. Learning shape models for monocular human pose estimation from the microsoft xbox kinect. In Computer Vision Workshops (ICCV Workshops), 2011 IEEE International Conference on, pages 1202-1208. IEEE, 2011.

[12] Carol E Chenoweth, Carolyn V Gould, and Sanjay Saint. Diagnosis, management, and prevention of catheter-associated urinary tract infections. Infectious Disease Clinics Of North America, 28(1):105-119, 2014.

[13] Carol E. Chenoweth and Sanjay Saint. Urinary tract infections. Infectious disease clinics of North America, 25(1):103-115, 03 2011.

[14] Elaine R Cohen, Joe Feinglass, Jeffrey H Barsuk, Cynthia Barnard, Anna O'Donnell, William C McGaghie, and Diane B Wayne. Cost savings from reduced catheter-related bloodstream infection after simulation-based education for residents in a medical intensive care unit. Simulation in Healthcare, 5(2):98-102, 2010.

[15] Kristian Damjker and Hassan Foroosh. Mesh-free sparse representation of multidimensional lidar data. Proc. IEEE International Conference on Image Processing (ICIP), 2014.

[16] Gregory A DeBourgh. Psychomotor skills acquisition of novice learners: A case for contextual learning. Nurse educator, 36(4):144-149, 2011.

[17] Paul Dietz and Darren Leigh. Diamondtouch: A multi-user touch technology. In Proceedings of the 14th Annual ACM Symposium on User Interface Software and Technology, UIST '01, pages 219-226, New York, N.Y., USA, 2001. ACM.

[18] Lorri Downs. Better together: Focusing on processes and compliance to prevent hospital acquired infections. Operating Room, June 2010.

[19] Ashley Flores. Sterile versus non-sterile glove use and aseptic technique. Nursing standard, 23(6):35-39, 2008.

[20] Centers for Disease Control and Prevention. Healthcare-associated infections (hais). www.cdc.gov/hai/surveillance/, October 2014.

[21] Hasbro Gaming. Operation Game. www.hasbro.com/games/enUS/shop/details. cfm?R=86309B1C-5056-9047-F544-77FCCCF4C38F:en_US, Jan. 9, 2014.

[22] Laura Gonzalez and Mary Lou Sole. Urinary catheterization skills: One simulated check is not enough. Clinical Simulation in Nursing, 10(9):455-460, 2014.

[23] Carolyn V. Gould, Craig A. Umscheid, Rajender K. Agarwal, Gretchen Kuntz, David A. Pegues, and the Healthcare Infection Control Practices Advisory Committee (HICPAC). Guideline for prevention of catheter-associated urinary tract infections, 2009. www.cdc.gov/hicpac/cauti/001_cauti.html, Dec. 29, 2009.

[24] Mikel Gray, D Newman, C Einhorn, and B Czarapata. Expert review: best practices in managing the indwelling catheter. Perspectives, 7(1):1-12, 2006.

[25] Jiseong Gu and Geehyuk Lee. Touchstring: A flexible linear multi-touch sensor for prototyping a freeform multi-touch surface. In Proceedings of the 24th Annual ACM Symposium Adjunct on User Interface Software and Technology, UIST '11 Adjunct, pages 75-76, New York, N.Y., USA, 2011. ACM.

[26] Yedid Hoshen, Gil Ben-Artzi, and Shmuel Peleg. Wisdom of the crowd in egocentric video curation. In The IEEE Conference on Computer Vision and Pattern Recognition (CVPR) Workshops, June 2014.

[27] R. Douglas Scott II. The direct medical costs of healthcare-associated infections in u.s. hospitals and the benefits of prevention. www.cdc.gov/HAI/pdfs/hai/Scott_CostPaper.pdf, March 2009.

[28] Adrian Ilie and Greg Welch. Online control of active camera networks for computer vision tasks. ACM Trans. Sen. Netw., 10(2):25:1-25:40, January 2014.

[29] Adrian Ilie, Greg Welch, and Marc Macenko. A stochastic quality metric for optimal control of active camera network configurations for 3d computer vision tasks. In Proceedings of ECCV 2008 workshop on Multi-camera and Multi-modal Sensor Fusion Algorithms and Applications, Marseille, France, Oct. 18, 2008. European Conference on Computer Vision (ECCV).

[30] Dumitru Adrian Ilie. On-Line Control of Active Camera Networks. Ph.d. dissertation, The University of North Carolina at Chapel Hill, Department of Computer Science, Chapel Hill, N.C., USA, December 2010.

[31] Shahram Izadi, Ankur Agarwal, Antonio Criminisi, John Winn, Andrew Blake, and Andrew Fitzgibbon. C-slate: A multi-touch and object recognition system for remote collaboration using horizontal surfaces. In Tabletop, pages 3-10. IEEE Computer Society, 2007.

[32] F. Janabi-Sharifi and M. Marey. A kalman-filter-based method for pose estimation in visual servoing. Robotics, IEEE Transactions on, 26(5):939-947, 2010.

[33] Imran Junejo, Xiaochun Cao, and Hassan Foroosh. Calibrating freely moving cameras. Proceedings of IAPR International Conference on Pattern Recognition (ICPR), pages 880-883, 2006.

[34] Imran Junejo, Xiaochun Cao, and Hassan Foroosh. Configuring mixed reality environment. Proceedings of IAPR International Conference on Pattern Recognition (ICPR), pages 884-887, 2006.

[35] Imran Junejo, Xiaochun Cao, and Hassan Foroosh. Geometry of a non-overlapping multicamera network. Proc. of IEEE International Conference on Advanced Video and Signal-based Surveillance (AVSS), pages 43-48, 2006.

[36] Imran Junejo, Xiaochun Cao, and Hassan Foroosh. Auto-configuration of a dynamic nonoverlapping camera network. IEEE Trans. Systems, Man, and Cybernetics, 37(4):803-816, 2007.

[37] Imran Junejo and Hassan Foroosh. Trajectory rectification and path modeling for surveillance. Proc. of International Conference on Computer Vision (ICCV), 2007.

[38] Imran Junejo and Hassan Foroosh. Euclidean path modeling for video surveillance. Image and Vision Computing, 26(4):512-528, 2008.

[39] Imran Junejo and Hassan Foroosh. Optimizing ptz camera calibration from two images. Machine Vision and Applications, 23(2):375-389, 2012.

[40] Imran N. Junejo, Adeel Bhutta, and Hassan Foroosh. Single-class svm for dynamic scene modeling. Signal Image and Video Processing, 7(1):45-52, 2013.

[41] Rudolph Emil Kalman. A new approach to linear filtering and prediction problems. Transactions of the ASME-Journal of Basic Engineering, 82(Series D):35-45, 1960.

[42] A. Karpathy, S. Miller, and Li Fei-Fei. Object discovery in 3d scenes via shape analysis. In Robotics and Automation (ICRA), 2013 IEEE International Conference on, pages 2088-2095, 2013.

[43] S. Khan, O. Javed, Z. Rasheed, and M. Shah. Human tracking in multiple cameras. In Computer Vision, 2001. ICCV 2001. Proceedings. Eighth IEEE International Conference on, volume 1, pages 331-336 vol. 1, 2001.

[44] Kitware. Vtk visualization toolkit. www.vtk.org, October 2014.

[45] Jennifer Lucado, Kathryn Paez, Roxanne Andrews, and Claudia Steiner. Statistical brief #94. adult hospital stays with infections due to medical care, 2007. Healthcare Cost and Utilization Project (HCUP), August 2010.

[46] Andrew Maimone and Henry Fuchs. Reducing interference between multiple structured light depth sensors using motion. In Proceedings of the 2012 IEEE Virtual Reality, VR '12, pages 51-54, Washington, D.C., USA, 2012. IEEE Computer Society.

[47] Jennifer Meddings, Sarah L. Krein, Mohamad G. Fakih, Russell N. Olmsted, and Sanjay Saint. Chapter 9. reducing unnecessary urinary catheter use and other strategies to prevent catheter associated urinary tract infections. In Making Health Care Safer II: An Updated Critical Analysis of the Evidence for Patient Safety Practices, number 211 in Evidence Report/Technology Assessment, pages 73-87. Agency for Healthcare Research and Quality (AHRQ), U.S. Department of Health and Human Services, March 2013.

[48] Thomas B. Moeslund and Erik Granum. A survey of computer vision-based human motion capture. Computer Vision and Image Understanding, 81(3):231-268, 2001.

[49] Mohammad Moghimi, Pablo Azagra, Luis Montesano, Ana C. Murillo, and Serge Belongie. Experiments on an RGB-D wearable vision system for egocentric activity recognition. In The IEEE Conference on Computer Vision and Pattern Recognition (CVPR) Workshops, June 2014.

[50] Juliette Mullin. A look at hospital infection rates in your state. www.advisory.com/daily-briefing/blog/2014/04/is-your-state-preventing-infections, October 2014.

[51] Richard A. Newcombe, Shahram Izadi, Otmar Hilliges, David Molyneaux, David Kim, Andrew J. Davison, Pushmeet Kohli, Jamie Shotton, Steve Hodges, and Andrew W. Fitzgibbon. Kinectfusion: Real-time dense surface mapping and tracking. In ISMAR, pages 127-136, 2011.

[52] National Healthcare Safety Network (NHSN). National healthcare safety network (nhsn) patient safety component. www.cdc.gov/nhsn/Training/patient-safety-component/, October 2014.

[53] Iason Oikonomidis, Nikolaos Kyriazis, and Antonis A Argyros. Efficient model-based 3d tracking of hand articulations using kinect. In BMVC, pages 1-11, 2011.

[54] Jia Pan, Sachin Chitta, and Dinesh Manocha. Probabilistic collision detection between noisy point clouds using robust classification. In International Symposium on Robotics Research, 2011.

[55] Jun Rekimoto. Smartskin: An infrastructure for freehand manipulation on interactive surfaces. In Proceedings of the SIGCHI Conference on Human Factors in Computing Systems, CHI '02, pages 113-120, New York, N.Y., USA, 2002. ACM.

[56] Sanjay Saint. Clinical and economic consequences of nosocomial catheter-related bacteriuria. American Journal of Infection Control, 28(1):68-75, 2000.

[57] Sanjay Saint. Chapter 15: Prevention of nosocomial urinary tract infections. In Making health care safer: A critical analysis of patient safety practices, pages 149-162. Agency for Healthcare Research and Quality, U.S. Department of Health and Human Services, 2001.

[58] David Sickinger et al. Augmented reality: Combining the artoolkit, itk, &vtk for use in a biomedical application. 2004.

[59] M. Teschner, S. Kimmerle, B. Heidelberger, G. Zachmann, L. Raghupathi, A. Fuhrmann, M.-P. Cani, F. Faure, N. Magnenat-Thalmann, W. Strasser, and P. Volino. Collision detection for deformable objects. Computer Graphics Forum, 24(1):61-81, 2005.

[60] Jing Tong, Jin Zhou, Ligang Liu, Zhigeng Pan, and Hao Yan. Scanning 3d full human bodies using kinects. Visualization and Computer Graphics, IEEE Transactions on, 18(4):643-650, 2012.

[61] Department of Computer Science UNC Chapel Hill. Virtual reality peripheral network. www.cs.unc.edu/Research/vrpn/, October 2014.

[62] Abraham Verghese. A doctor's touch. www.ted.com/talks/abraham_verghese_a_doctor_s_touch.html, Jul. 14, 2011.

[63] Catharine M Walsh, Donald N Rose, Adam Dubrowski, Simon C Ling, Lawrence E M Grierson, David Backstein, and Heather Carnahan. Learning in the simulated setting: a comparison of expert-, peer-, and computer-assisted learning. Academic Medicine, 86(10):S12-S16, 2011.

[64] Colin Ware. Information visualization: perception for design. Elsevier, 2013.

[65] A. Weiss, D. Hirshberg, and M. J. Black. Home 3D body scans from noisy image and range data. In Int. Conf. on Computer Vision (ICCV), pages 1951-1958, Barcelona, November 2011. IEEE.

[66] Greg Welch and Gary Bishop. An introduction to the Kalman filter. Technical Report TR95-041, University of North Carolina at Chapel Hill, Department of Computer Science, 1995.

[67] Lu Xia, Chia-Chih Chen, and J. K. Aggarwal. Human detection using depth information by kinect. In Computer Vision and Pattern Recognition Workshops (CVPRW), 2011 IEEE Computer Society Conference on, pages 15-22, 2011.

[68] Chenyang Xu and Jerry L Prince. Snakes, shapes, and gradient vector flow. Image Processing, IEEE Transactions on, 7(3):359-369, 1998.

[69] Jinghe Zhang, Greg Welch, and Gary Bishop. Observability and estimation uncertainty analysis for pmu placement alternatives. (under submission), 2010.

[70] Huiyu Zhou and Huosheng Hu. A survey—human movement tracking and stroke rehabilitation, 2004.

[71] Eyal Zimlichman, Daniel Henderson, Orly Tamir, Calvin Franz, Peter Song, Cyrus K. Yamin, Carol Keohane, Charles R. Denham, and David W. Bates. Health care-associated infections: A meta-analysis of costs and financial impact on the us health care system. JAMA Internal Medicine, 173(22):2039-2046, 2013.

The contents of references 1-71 are hereby incorporated by reference in their entirety.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A system for monitoring a sterile field associated with a medical procedure, the system comprising:
   at least one sensor being adjacent an area where the medical procedure is to be performed;
   said at least one sensor configured to monitor at least the area, a patient for the medical procedure, and a medical technician for the medical procedure;
   a processor coupled to said at least one sensor and configured to
   generate a spatial model of the area, the spatial model comprising a plurality of elements,
   generate a contamination probability value for each element of the spatial model, and
   detect a sterile field event, and an associated location for the sterile field event; and
   an output device coupled to said processor and configured to generate an alert indicator when the sterile field event is detected, the alert indicator also including the associated location.

2. The system of claim 1 wherein said at least one sensor comprises an image sensor configured to generate at least one of image data and depth data for the sterile field event.

3. The system of claim 1 further comprising at least one tag coupled to at least one of a device associated with the medical procedure, the patient, and the medical technician; and wherein said at least one sensor is configured to detect a location of the at least one of the device associated with the medical procedure, the patient, and the medical technician via an associated tag.

4. The system of claim 1 wherein said output device comprises a display; and wherein said processor is configured to generate indicators of elements having respective contamination probability values exceeding a threshold using said display.

5. The system of claim 1 wherein said processor is configured to iteratively update the contamination probability value for each element of the spatial model during the medical procedure.

6. The system of claim 1 wherein said processor is configured to:
   generate a gap value between adjacent elements in the plurality of elements of the spatial model; and
   when one of the adjacent elements is contaminated and the gap value is less than a threshold gap value, indicate the other element also as contaminated.

7. The system of claim 1 wherein said processor is configured to detect the sterile field event comprising at least one of a violation and a risk of violation of the sterile field.

8. A system for monitoring a sterile field associated with a medical procedure, the system comprising:
   at least one sensor being adjacent an area where the medical procedure is to be performed;
   said at least one sensor configured to monitor at least the area, a patient for the medical procedure, and a medical technician for the medical procedure;
   at least one tag coupled to at least one of a device associated with the medical procedure, the patient, and the medical technician;
   said at least one sensor is configured to detect a location of the at least one of the device, the patient, and the medical technician via an associated tag;
   a processor coupled to said at least one sensor and configured to
   generate a spatial model of the area, the spatial model comprising a plurality of elements,
   generate a contamination probability value for each element of the spatial model, and
   detect a sterile field event, and an associated location for the sterile field event within the spatial model, the sterile field event comprising at least one of a violation and a risk of violation of the sterile field; and
   an output device coupled to said processor and configured to generate an alert indicator when the sterile field event is detected, the alert indicator also including the associated location.

9. The system of claim 8 wherein said at least one sensor comprises an image sensor configured to generate at least one of image data and depth data for the sterile field event.

10. The system of claim 8 wherein said output device comprises a display; and wherein said processor is configured to generate indicators of elements having respective contamination probability values exceeding a threshold using said display.

11. The system of claim 10 wherein said processor is configured to iteratively update the contamination probability value for each element of the spatial model during the medical procedure.

12. The system of claim 8 wherein said processor is configured to:
generate a gap value between adjacent elements in the plurality of elements of the spatial model; and
when one of the adjacent elements is contaminated and the gap value is less than a threshold gap value, indicate the other element also as contaminated.

13. A method for operating a system for monitoring a sterile field associated with a medical procedure, the method comprising:
operating at least one sensor being adjacent an area where the medical procedure is to be performed and to monitor at least the area, a patient for the medical procedure, and a medical technician for the medical procedure;
operating a processor coupled to the at least one sensor and to
generate a spatial model of the area, the spatial model comprising a plurality of elements,
generate a contamination probability value for elements of the spatial model, and
detect a sterile field event, and an associated location for the sterile field event; and
operating an output device coupled to the processor and to generate an alert indicator when the sterile field event is detected, the alert indicator also including the associated location.

14. The method of claim 13 further comprising generating at least one of image data and depth data for the sterile field event.

15. The method of claim 13 further comprising operating at least one tag coupled to at least one of a device associated with the medical procedure, the patient, and the medical technician, and operating the at least one sensor to detect a location of the device, the patient, and the medical technician.

16. The method of claim 13 wherein the output device comprises a display; and further comprising operating the processor to generate indicators of elements having respective contamination probability values exceeding a threshold using the display.

17. The method of claim 13 further comprising operating the processor to iteratively update the contamination probability value for each element of the spatial model during the medical procedure.

18. The method of claim 13 further comprising operating the processor to:
generate a gap value between adjacent elements in the plurality of elements of the spatial model; and
when one of the adjacent elements is contaminated and the gap value is less than a threshold gap value, indicate the other element also as contaminated.

19. The method of claim 13 further comprising operating the processor to detect the sterile field event comprising at least one of a violation and a risk of violation of the sterile field.

* * * * *